US012667618B2

(12) United States Patent
Lee et al.

(10) Patent No.: US 12,667,618 B2
(45) Date of Patent: Jun. 30, 2026

(54) POLYMER NANOPARTICLE COMPOSITION FOR INDUCING IMMUNITY AND PREPARATION METHOD THEREFOR

(71) Applicant: SAMYANG HOLDINGS CORPORATION, Seoul (KR)

(72) Inventors: So Jin Lee, Seoul (KR); Joon Young Park, Seoul (KR); Hye Yeong Nam, Seongnam-si (KR); He Len Cho, Seongnam-si (KR); Goo Young Kim, Yongin-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 969 days.

(21) Appl. No.: 17/774,887

(22) PCT Filed: Nov. 5, 2020

(86) PCT No.: PCT/KR2020/015435
§ 371 (c)(1),
(2) Date: May 6, 2022

(87) PCT Pub. No.: WO2021/091272
PCT Pub. Date: May 14, 2021

(65) Prior Publication Data

US 2022/0409710 A1 Dec. 29, 2022

(30) Foreign Application Priority Data

Nov. 7, 2019 (KR) ........................ 10-2019-0141745

(51) Int. Cl.

*A61K 47/50* (2017.01)
*A61K 39/00* (2006.01)
*A61K 39/39* (2006.01)
*A61P 35/00* (2006.01)

(52) U.S. Cl.

CPC .............. *A61K 47/50* (2017.08); *A61K 39/00* (2013.01); *A61K 39/001156* (2018.08); *A61K 39/00119* (2018.08); *A61K 39/39* (2013.01); *A61P 35/00* (2018.01); *A61K 2039/53* (2013.01); *A61K 2039/55555* (2013.01); *A61K 2039/572* (2013.01); *A61K 2039/6093* (2013.01)

(58) Field of Classification Search

CPC .. A61K 47/50; A61K 39/00119; A61K 39/39; A61K 39/001156; A61K 39/00; A61K 2039/53; A61K 2039/55555; A61K 2039/572; A61K 2039/6093; A61P 35/00
See application file for complete search history.

(56) References Cited

U.S. PATENT DOCUMENTS

| | | | |
|---|---|---|---|
| 2016/0193348 A1 | 7/2016 | Choi et al. | |
| 2018/0250409 A1 | 9/2018 | Nam et al. | |
| 2018/0344638 A1 | 12/2018 | Nam et al. | |
| 2019/0060446 A1 | 2/2019 | Gao et al. | |

FOREIGN PATENT DOCUMENTS

| | | | | |
|---|---|---|---|---|
| EP | 2377517 A2 | 10/2011 | | |
| JP | 2015-514076 A | 5/2015 | | |
| JP | 2018-526321 A | 9/2018 | | |
| KR | 10-2011-0077818 A | 7/2011 | | |
| KR | 10-2014-0141229 A | 12/2014 | | |
| KR | 10-2017-0032858 A | 3/2017 | | |
| KR | 10-2017-0073528 A | 6/2017 | | |
| KR | 10-2018-0052083 A | 5/2018 | | |
| KR | 10-2018-0114946 A | 10/2018 | | |
| KR | 10-2019-0024849 A | 3/2019 | | |
| WO | WO 2005/035606 A1 | 4/2005 | | |
| WO | WO 2013/143683 A1 | 10/2013 | | |
| WO | WO 2013151326 | * 10/2013 | | ........... A61K 9/1075 |
| WO | WO 2016/176330 A1 | 11/2016 | | |
| WO | WO 2017161096 | * 9/2017 | | |

OTHER PUBLICATIONS

International Search Report, issued in PCT/KR2020/015435, mailed Feb. 9, 2021.
Extended European Search Report for European Application No. 20885383.8, dated Nov. 6, 2023.
Hamdy et al., "Co-delivery of cancer-associated antigen and Toll-like receptor 4 ligand in PLGA nanoparticles induces potent CD8+ T cell-mediated anti-tumor immunity", Vaccine, vol. 26, No. 39, available online on Aug. 3, 2008, pp. 5046-5057.
Oberli et al., "Lipid Nanoparticle Assisted mRNA Delivery for Potent Cancer Immunotherapy", NANO Letters, vol. 17, No. 3, published on Nov. 23, 2016, pp. 1326-1335.
Xu et al., "Multifunctional nanoparticles co-delivering Trp2 peptide and CpG adjuvant induce potent cytotoxic T-lymphocyte response against melanoma and its lung metastasis," Journal of Controlled Release, vol. 172, No. 1, available online on Sep. 1, 2013, pp. 259-265.
Indian Examination Report for Indian Application No. 202247031618, dated Feb. 18, 2025, with a partial English translation.

* cited by examiner

*Primary Examiner* — Shirley V Gembeh
(74) *Attorney, Agent, or Firm* — Birch, Stewart, Kolasch & Birch, LLP

(57) ABSTRACT

Disclosed are a composition for inducing immunity against an active ingredient and a method for preparing same, the composition comprising: a nucleic acid, a polypeptide, or a combination thereof as the active ingredient; a cationic compound; an amphiphilic block copolymer; and a polylactate, wherein the active ingredient is encapsulated in a nanoparticle structure formed by the amphiphilic block copolymer and the polylactate.

16 Claims, 5 Drawing Sheets

【FIGURE 1】
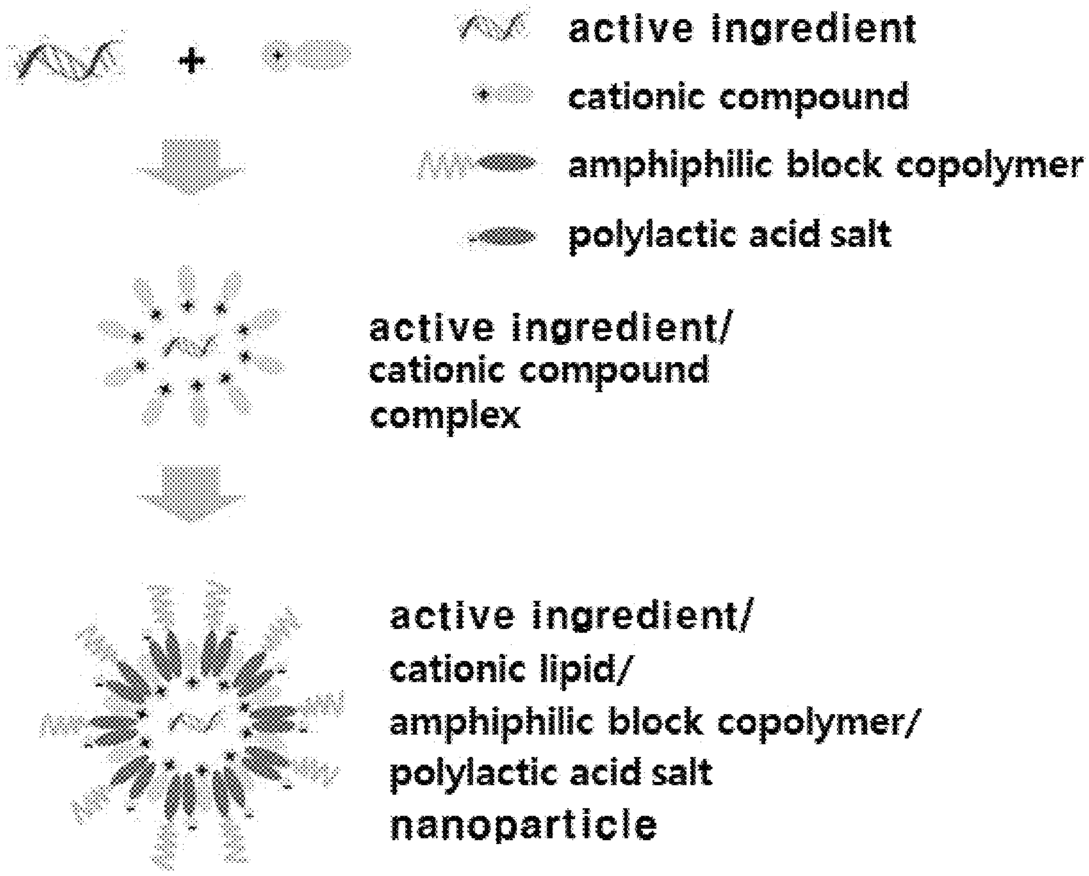

【FIGURE 2】
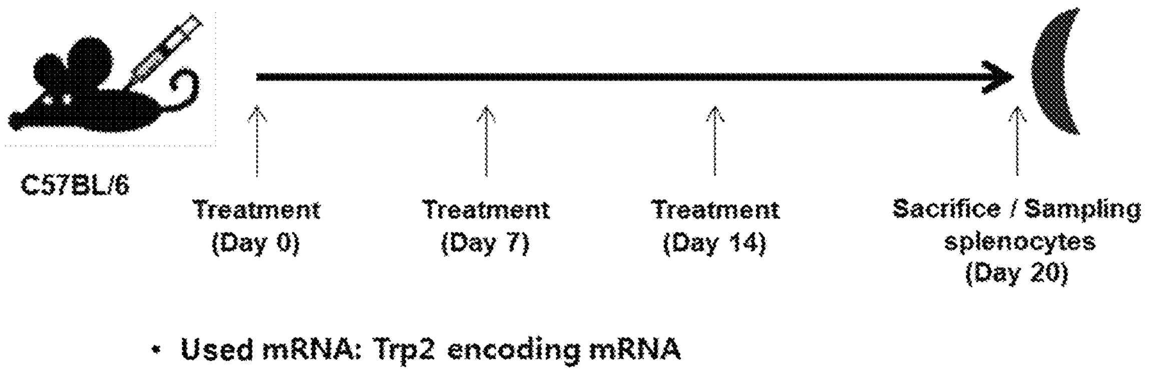
【FIGURE 3】
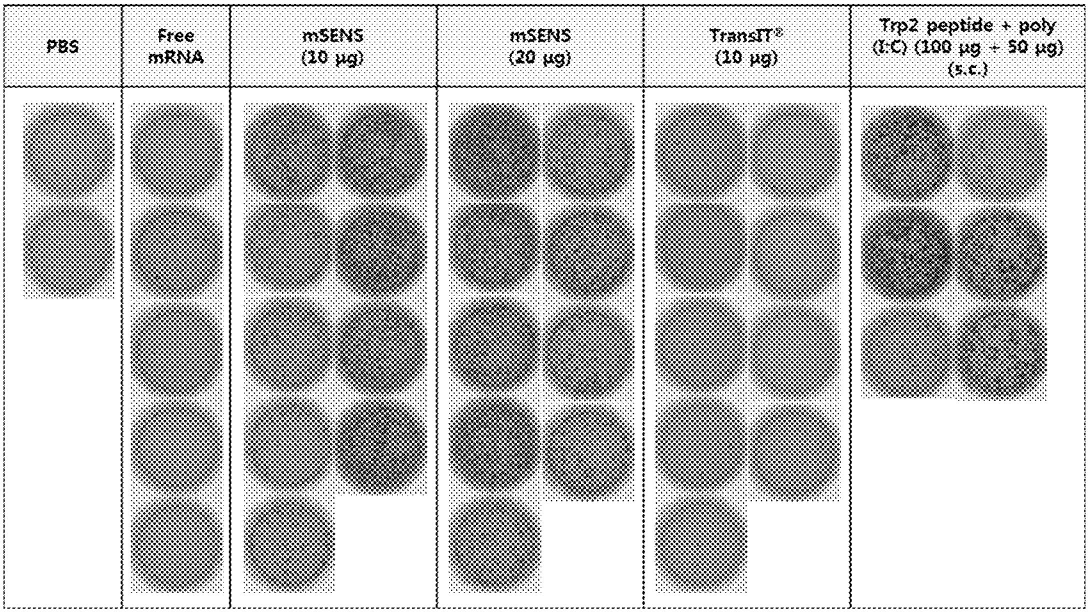

【FIGURE 4】
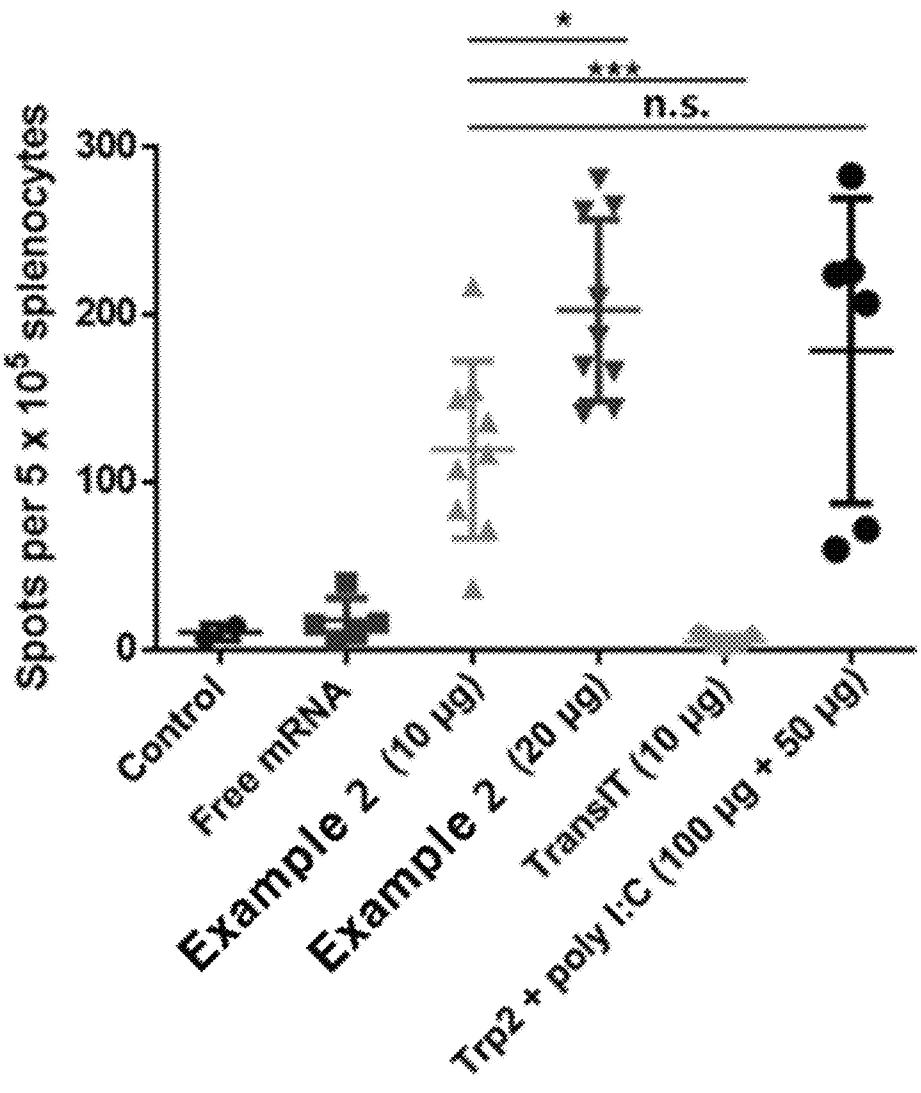

【FIGURE 5】
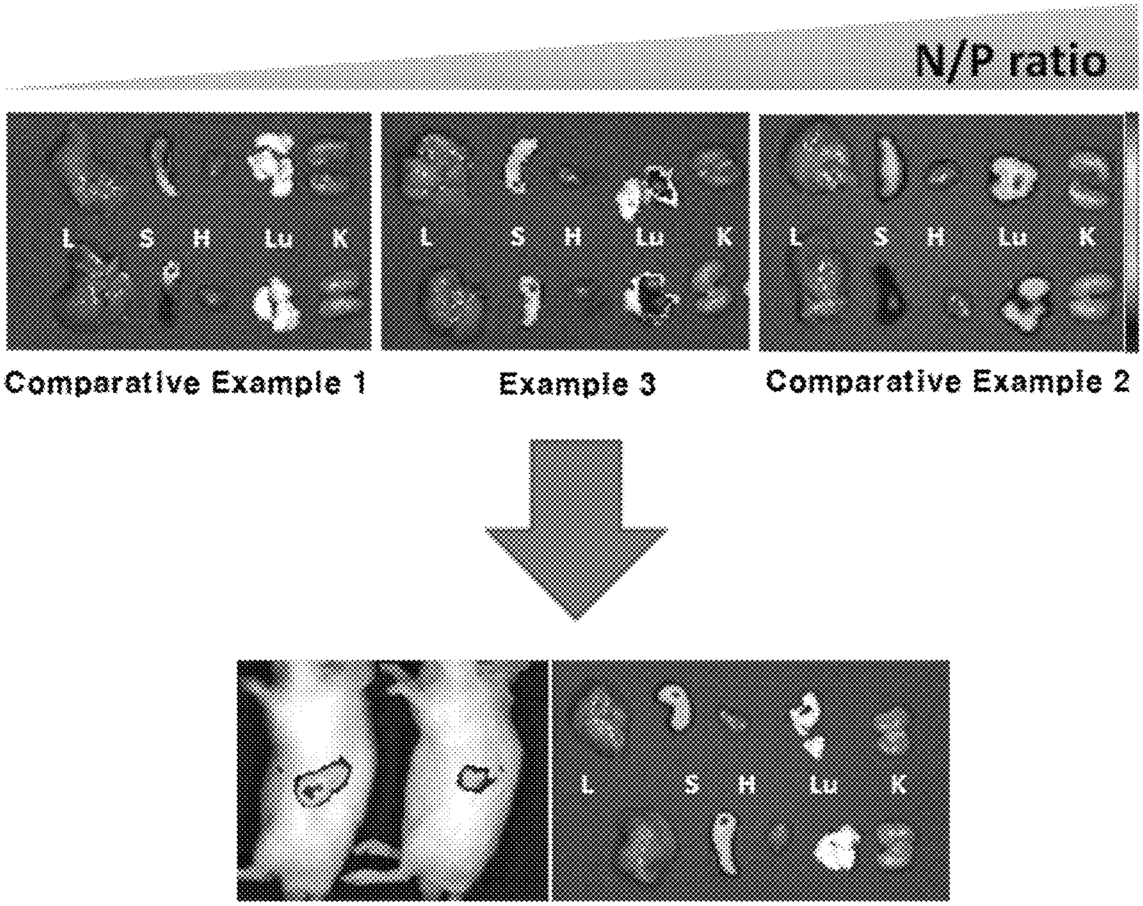

【FIGURE 6】
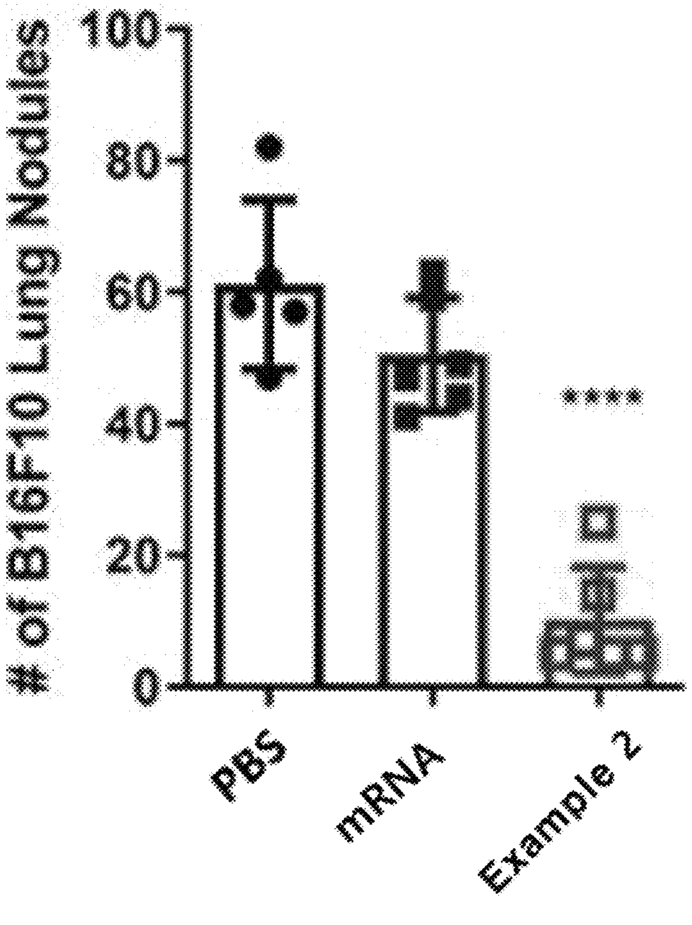

POLYMER NANOPARTICLE COMPOSITION FOR INDUCING IMMUNITY AND PREPARATION METHOD THEREFOR

TECHNICAL FIELD

This disclosure relates to a polymer nanoparticle composition capable of inducing immunity and a method for preparing the same, and more particularly, to a vaccine composition for treating or preventing disease that effectively induces T-cell immunity to an antigen.

BACKGROUND ART

Safe and efficient drug delivery technologies have been studied for a long time for treatment using anionic drugs including nucleic acid, and various delivery systems and delivery technologies have been developed. The delivery systems are largely divided into a viral delivery system using adenovirus or retrovirus, etc. and a non-viral delivery system using cationic lipids and cationic polymers. A technology using a viral delivery system is exposed to risks such as non-specific immune reaction, etc., and it is known to have many problems in commercialization due to the complex production process. Therefore, recent studies have progressed toward a non-viral delivery system to overcome these disadvantages. Compared to the viral delivery system, the non-viral delivery system has the advantages of fewer side effects in terms of in vivo safety and a low production price in terms of economic feasibility.

On the other hand, the development of a cancer antigen vaccine that induces an antigen-specific T-cell response as an anticancer treatment is actively progressing (npj Vaccines vol. 4, Article number: 7 (2019)). In order to induce an effective anticancer immune response, it is necessary to deliver cancer antigens to antigen-presenting cells and to effectively stimulate cytotoxic T-cells by increasing the presentation rate of tumor-specific antigen-derived epitopes. For efficient antigen delivery, methods for inducing an antigen-specific immune response using either tumor cells themselves as antigens, or peptides, nucleic acids, viruses or dendritic cells as antigens are being used (Advances in Cancer Research Vol. 119), 2013, 421-475). In particular, mRNA among nucleic acids is a non-infectious, non-insertable platform that has relatively few risks, such as mutated genes, and has the advantage of being rapidly and economically manufacturable in large quantities through in vitro transcription reactions. Therefore, it stands out as a platform for personalized anticancer vaccines for various types of cancer along with infectious diseases (Nat Rev Drug Discov. 2018 April; 17(4): 261-279).

Korean Patent Application Laid-Open No. 10-2017-0032858 discloses a composition for delivering an anionic drug, comprising the anionic drug as an active ingredient; a cationic compound; an amphiphilic block copolymer, wherein the anionic drug forms a complex with the cationic compound by electrostatic interaction, and the complex is entrapped in the nanoparticle structure of the amphiphilic block copolymer and the salt of polylactic acid and a method for preparing the same. However, only the use of an anionic drug as a delivery system is disclosed herein, and the effect on the subject's immunity is not disclosed.

CONTENTS OF THE INVENTION

Problems to be Solved

The purpose of the present invention is to provide a composition for inducing immunity to an active ingredient, comprising: a nucleic acid, a polypeptide or a combination thereof as the active ingredient; a cationic compound; an amphiphilic block copolymer; and a salt of polylactic acid, wherein the active ingredient is entrapped in the nanoparticle structure of the amphiphilic block copolymer and the salt of polylactic acid and a method for preparing the same.

Technical Means to Solve the Problems

A first aspect of the present invention provides a composition for inducing immunity to an active ingredient, comprising: a nucleic acid, a polypeptide or a combination thereof as the active ingredient; a cationic compound; an amphiphilic block copolymer; and a salt of polylactic acid, wherein the active ingredient is entrapped in the nanoparticle structure of the amphiphilic block copolymer and the salt of polylactic acid.

Another aspect of the present invention provides a method for preparing a composition for inducing immunity to the active ingredient, comprising (a) mixing an aqueous solution containing an active ingredient, which is a nucleic acid, a polypeptide or a combination thereof, with a solution in which a cationic compound is dissolved in a water-miscible organic solvent; (b) mixing an aqueous solution of the amphiphilic block copolymer and a salt of polylactic acid with the mixture of step (a); (c) adding an aqueous solvent to the mixture of step (b) and mixing them; and (d) removing the solvent from the mixture of step (c).

Effects of the Invention

The composition for inducing immunity according to the present invention can induce immunity of an individual to an active ingredient such as a nucleic acid, a polypeptide or a combination thereof, and has the advantage of effectively inducing immunity even if the active ingredient is difficult to recognize as an antigen. Using this, the composition for inducing immunity can be used as an autologous cancer vaccine, and it ultimately can be used for preventing or treating cancer.

In one embodiment, the composition for inducing immunity according to the present invention can induce immunity to the active ingredient by delivering the active ingredient as described above to the spleen effectively.

BRIEF EXPLANATION OF THE DRAWINGS

FIG. 1 is a drawing showing a schematic structure of a composition for inducing immunity according to an embodiment of the present invention.

FIG. 2 is a schematic diagram of the animal test method of Example 2.

FIG. 3 is an image showing the expression level of IFN-γ in splenocytes by the composition for induction of immunity according to an embodiment of the present invention.

FIG. 4 is an ELISPOT graph showing the expression level of IFN-γ in splenocytes by the composition for inducing immunity according to an embodiment of the present invention.

FIG. 5 is an image showing the organ-specific expression of the composition for inducing immunity according to an embodiment of the present invention.

FIG. 6 is a graph showing the cancer treatment effect of the composition for inducing immunity according to an embodiment of the present invention.

MODES FOR THE INVENTION

Hereinafter, the present invention will be explained in detail.

Among the components of the composition according to the present invention, nucleic acids, polypeptides, or combinations thereof, which are active ingredients, may be related to antigens capable of inducing an immune response. For example, the nucleic acid may express an antigen, and in another example, the polypeptide may be recognized as an antigen.

The active ingredient may form a complex through electrostatic interaction with the cationic compound, and the complex may be entrapped in the nanoparticle structure formed by the amphiphilic block copolymer and the salt of polylactic acid. An exemplary structure thereof is schematically shown in FIG. 1.

Regarding the above nanoparticles, in an aqueous environment, the hydrophilic portion of the amphiphilic block copolymer forms the outer wall of the nanoparticles, and the hydrophobic portion of the amphiphilic block copolymer and the salt of polylactic acid contained as a separate component of the amphiphilic block copolymer form the inner wall of the nanoparticles, and the complex of the active ingredient and the cationic compound may be entrapped inside the formed nanoparticles. This nanoparticle structure improves the stability of the active ingredient in blood or body fluid.

The "nucleic acid" may be, for example, DNA, RNA, siRNA, shRNA, miRNA, mRNA, aptamer, antisense oligonucleotide or a combination thereof, but is not limited thereto. The nucleic acid expresses an antigen through a series of processes in the body, and may encode an antigen. For example, the nucleic acid may be DNA, RNA or mRNA comprising a nucleotide sequence of an antigen or encoding such a polypeptide sequence.

The "polypeptide" may be one that can be recognized as an antigen. The polypeptide may refer to a protein that can be recognized as an antigen through a series of processes in the body, including the polypeptide sequence of an antigen, an analog or a precursor thereof.

The composition for inducing immunity according to one embodiment has an effect of delivering an antigen into the body effectively, thereby treating or preventing a disease related to the antigen. For example, when the disease is a tumor, the nucleic acid may be one expressing a tumor antigen, or the polypeptide may be a tumor antigen. Examples of tumor antigen include Trp2 (tyrosinase-related protein 2), gp100 (Glycoprotein 100), tyrosinase, PSA (Prostate-specific antigen), WT1 (Wilms' tumor 1), MAGE-1 (Melanoma-associated antigen 1), NY-ESO-1 (cancer-testis antigen), MUC-1 (Mucin 1), etc. may be included, but are not limited thereto.

The composition for inducing immunity of the present invention has an efficient and excellent vaccine effect by allowing antigens that are difficult to induce immune induction to successfully occur even if a general administration method or carrier is used, and as a result, it may have an effect of treating diseases according to induction of immunity.

In another embodiment, the polypeptide may be a viral envelope, a glycoprotein, a bacterium, a cancer cell or a fragment thereof. In this case, the composition for inducing immunity of the present invention may be for treating or preventing diseases caused by viruses, bacteria or cancer cells.

The disease includes, but is not limited to, cancer, viral infection, cellular infection, allergy and the like. The composition for inducing immunity may be used as a vaccine for preventing diseases.

The nucleic acid or polypeptide as the active ingredient may have its backbone, amino acid, sugar or base which is chemically modified or the terminal thereof which is modified in order to increase blood stability or enhance the immune-inducing effect.

In one embodiment, the particle size of the nanoparticles may be defined as a Z-average value—for example, 800 nm or less, 600 nm or less, 500 nm or less, 400 nm or less, 300 nm or less, 200 nm or less or 150 nm or less, and may be 10 nm or more. In one embodiment, the particle size of the nanoparticles, defined as the Z-average value is, for example, 10 to 800 nm, 10 to 600 nm, 10 to 500 nm, 10 to 400 nm, 10 to 300 nm, 10 to 200 nm or 10 to 150 nm.

The "Z-average" may mean an average of hydrodynamic diameters of particle distributions measured using dynamic light scattering (DSL). The nanoparticles have a monodisperse particle distribution, and the polydispersity index may be, for example, 0.01 to 0.30, 0.05 to 0.25 or 0.1 to 0.2.

Also, in one embodiment, the surface charge of the nanoparticles may be, for example, −40 mV or more, −30 mV or more, −20 mV or more or −10 mV or more, and may be 40 mV or less, 30 mV or less, 20 mV or less or 10 mV or less. In one embodiment, the surface charge of the nanoparticles may be, for example, −40 to 40 mV, −30 to 30 mV, −20 to 20 mV or −10 to 10 mV. The surface charge may be measured in an environment close to a biological environment—for example, in 10 mM HEPES buffer (pH 7.2).

When the particle size and surface charge of the nanoparticles are maintained at the above levels, it is preferable in terms of stability of the nanoparticle structure, content of components, absorption in the body, and ease of sterilizing as a pharmaceutical composition. For example, when the active ingredient is a nucleic acid, one or more terminals of the nucleic acid may be modified with one or more selected from the group consisting of cholesterol, tocopherol and fatty acids having 10 to 24 carbon atoms. The cholesterol, tocopherol and fatty acids having 10 to 24 carbon atoms include their analogs, derivatives and metabolites of the cholesterol, the tocopherols and the fatty acids.

The content of the active ingredient may be, for example, 30 wt % or less, 25 wt % or less, 20 wt % or less, 15 wt % or less, 10 wt % or less or 5 wt % or less, and may be 0.05 wt % or more, 0.1 wt % or more, 0.25 wt % or more, 0.5 wt % or more or 1 wt % or more, based on the total weight of the composition. In one embodiment, the content of the active ingredient may be, for example, 0.05 to 30 wt %, 0.1 to 25 wt %, 0.25 to 20 wt %, 0.5 to 15 wt %, 1 to 10 wt % or 1 to 5 wt %, based on the total weight of the composition. If the content of the active ingredient is less than the above range based on the weight of the total composition, the amount of the delivery systems used compared to the drug is too large, so there may be side effects due to the delivery systems. If the content of the active ingredient exceeds the above range, the size of the nanoparticles is too large and the stability of nanoparticles is reduced, and there is a risk that the loss rate during filter sterilization may increase.

In a specific embodiment, the cationic compound may be a cationic lipid or a cationic polymer, and more specifically, a cationic lipid.

In one embodiment, the cationic lipid may be one or a combination of two or more selected from the group consisting of N,N-dioleyl-N,N-dimethylammoniumchloride (DODAC), N,N-distearyl-N,N-dimethylammoniumbromide (DDAB), N-(1-(2,3-dioleoyloxy)propyl-N,N,N-trimethylammoniumchloride (DOTAP), N,N-dimethyl-(2,3-dioleoyloxy)propylamine (DODMA), N,N,N-trimethyl-(2,3-dioleoyloxy)propylamine (DOTMA), 1,2-diacyl-3- trimethylammonium-propane (TAP), 1,2-diacyl-3-dimethylammonium-propane (DAP), 3β-[(N',N',N'-trimethylaminoethane)carbamoyl]cholesterol (TC-cholesterol), 3β-[N—(N',N'-dimethylaminoethane) carbamoyl]cholesterol (DC-cholesterol), monomethylaminoethane)carbamoyl]cholesterol (MC-cholesterol), 3β-[3β-(aminoethane)carbamoyl]cholesterol (AC-cholesterol), cholesteryloxypropane-1-amine (COPA), N—(N'-aminoethane)carbamoylpropanoic tocopherol (AC-tocopherol) and N—(N'-methylaminoethane)carbamoylpropanoic tocopherol (MC-tocopherol).

If such a cationic lipid is used, in order to decrease toxicity induced by cationic lipid, it may be preferable to use less polycationic lipid having high charge density, and more specifically, it is preferable to use a cationic lipid having one functional group capable of exhibiting positive charge per molecule in an aqueous solution.

Therefore, in a preferable embodiment, the cationic lipid may be at least one selected from the group consisting of 3β-[N—(N',N',N'-trimethylaminoethane)carbamoyl]cholesterol (TC-cholesterol), 3β-[N—(N',N'-dimethylaminoethane)carbamoylcholesterol (DC-cholesterol), 3β-[N—(N'-monomethylaminoethane)carbamoy]cholesterol (MC-cholesterol), 3β[N-(aminoethane)carbamoylcholesterol (AC-cholesterol), N-(1-(2,3-dioleoyloxy)propyl-N,N,N-trimethylammoniumchloride (DOTAP), N,N-dimethyl-(2,3-dioleoyloxy)propylamine (DODMA) and N,N,N-trimethyl-(2,3-dioleoyloxy)propylamine (DOTMA).

On the other hand, in one embodiment, the cationic polymer may be at least one selected from the group consisting of chitosan, glycol chitosan, protamine, polylysine, polyarginine, polyamidoamine (PAMAM), polyethylenimine, dextran, hyaluronic acid, albumin, polymer polyethylenimine (PEI), polyamine and polyvinylamine (PVAm), and more specifically, may be at least one selected from polymer polyethylenimine (PEI), polyamine and polyvinylamine (PVAm).

In one embodiment, the cationic lipid may be represented by the following Formula 1:

[Formula 1]

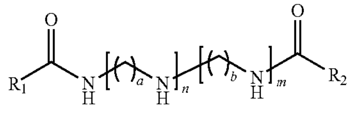

wherein each of n and m is 0 to 12 with the proviso that $2 \leq n+m \leq 12$, each of a and b is 1 to 6, and each of $R_1$ and $R_2$ is independently selected from the group consisting of saturated and unsaturated hydrocarbons having 11 to 25 carbon atoms.

More specifically, in Formula 1, each of n and m may be independently 1 to 9, and $2 \leq n+m \leq 10$.

More specifically, in Formula 1, each of a and b may be 2 to 4.

More specifically, each of $R_1$ and $R_2$ in Formula 1 may be independently selected from the group consisting of lauryl, myristyl, palmityl, stearyl, arachidyl, behenyl, lignoceryl, cerotyl, myristoleyl, palmitoleyl, sapienyl, oleyl, linoleyl, arachidonyl, eicosapentaenyl, erucyl, docosahexaenyl and cerotyl.

In one embodiment, the cationic lipid may be one or more selected from the group consisting of 1,6-dioleoyl triethylenetetramide(N,N'-((ethane-1,2-diylbis(azanediyl))bis(ethane-2,1-diyl))dioleamide), 1,8-dilinoleoyl tetraethylenepentamide ((9Z,9'Z,12Z,12'Z)—N,N'-(((azanediylbis(ethane-2,1-diyl))bis(azanediyl))bis(ethane-2,1-diyl))bis(octadeca-9,12-dienamide)), 1,4-dimyristoleoyl diethylenetriamide((9Z,9'Z)—N,N'-(azanediylbis(ethane-2,1-diyl))bis(tetradec-9-enamide)), 1,10-distearoyl pentaethylenehexamide (N,N'-(3,6,9,12-tetraazatetradecane-1,14-diyOdistearamide) and 1,10-dioleoyl pentaethylenehexamide (N,N'-(3,6,9,12-tetraazatetradecane-1,14-diyOdioleamide).

The content of the cationic compound in the composition for inducing immunity of the present invention may be, for example, 25 parts by weight or less, 20 parts by weight or less, 18 parts by weight or less, 15 parts by weight or less, 12 parts by weight or less, 10 parts by weight or less or 8 parts by weight or less, and may be 1 part by weight or more, 1.5 parts by weight or more, 2 parts by weight or more, 2.5 parts by weight or more or 3 parts by weight or more, based on 1 part by weight of the active ingredient. In one embodiment, the content of the cationic compound in the composition may be, 1 to 25 parts by weight, 1.5 to 10 parts by weight, 2 to 15 parts by weight, 2.5 to 10 parts by weight or 3 to 8 parts by weight, based on 1 part by weight of the active ingredient. If the content of the cationic compound in the composition is less than the above range, it may not be possible to form a stable complex with the active ingredient. If the content of the cationic compound exceeds the above range, the size of the nanoparticles is too large, the stability is lowered, and there is a risk that the loss rate during filter sterilization may increase.

When the active ingredient is a nucleic acid, the cationic compound and the nucleic acid are combined by electrostatic interaction to form a complex. In one embodiment, the ratio of the amount of electric charge of the nucleic acid (P) and the cationic compound (N) (N/P; ratio of the cationic charge of the cationic compound to the anionic charge of the nucleic acid) may be 0.5 or more, 1 or more, 2 or more or 3 or more, and may be 100 or less, 50 or less, 20 or less or 10 or less—for example, 0.5 to 100, 1 to 50, 2 to 20, 2 to 15, or 3 to 10. If the ratio (N/P) is less than 0.5, it may be difficult to form a complex including a sufficient amount of nucleic acid, whereas if the ratio (N/P) exceeds 100, there is a risk of causing toxicity. In addition, the N/P value may play an important role in the specific expression of the active ingredient in the spleen.

In one embodiment, the amphiphilic block copolymer may be an A-B type block copolymer including a hydrophilic A block and a hydrophobic B block. The A-B type block copolymer forms a core-shell type polymeric nanoparticle in an aqueous solution, wherein the hydrophobic B block forms a core (an inner wall) and the hydrophilic A block forms a shell (an outer wall).

In one embodiment, the hydrophilic A block may be at least one selected from the group consisting of polyalkyleneglycol, polyvinyl alcohol, polyvinyl pyrrolidone, polyacrylamide and derivatives thereof.

More specifically, the hydrophilic A block may be at least one selected from the group consisting of monomethoxy polyethylene glycol, monoacetoxy polyethylene glycol, polyethylene glycol, a copolymer of polyethylene and propylene glycol, and polyvinyl pyrrolidone.

In one embodiment, the hydrophilic A block may have a number average molecular weight of 200 to 50,000 Dalton, more specifically 1,000 to 20,000 Dalton, and much more specifically 1,000 to 5,000 Dalton.

If necessary, a functional group or a ligand that can reach to a specific tissue or cell, or a functional group capable of promoting intracellular delivery may be chemically conjugated to the terminal of the hydrophilic A block so as to control the distribution of the polymeric nanoparticle delivery system which is formed from the amphiphilic block copolymer and the salt of polylactic acid in a body, or to increase the efficiency of delivery of the nanoparticle delivery system into cells. In one embodiment, the functional group or ligand may be at least one selected from the group consisting of monosaccharide, polysaccharide, vitamins, peptides, proteins and an antibody to a cell surface receptor. In more specific examples, the functional group or ligand may be at least one selected from the group consisting of anisamide, vitamin B9 (folic acid), vitamin B12, vitamin A, galactose, lactose, mannose, hyaluronic acid, RGD peptide, NGR peptide, transferrin, an antibody to a transferrin receptor, etc.

The hydrophobic B block is a biocompatible and biodegradable polymer, and in one embodiment, it may be at least one selected from the group consisting of polyester, polyanhydride, polyamino acid, polyorthoester and polyphosphazine.

More specifically, the hydrophobic B block may be at least one selected from the group consisting of polylactide, polyglycolide, polycaprolactone, polydioxane-2-one, a copolymer of polylactide and glycolide, a copolymer of polylactide and polydioxane-2-one, a copolymer of polylactide and polycaprolactone, and a copolymer of polyglycolide and polycaprolactone.

In one embodiment, the hydrophobic B block may have a number average molecular weight of 50 to 50,000 Dalton, more specifically 200 to 20,000 Dalton, and much more specifically 1,000 to 5,000 Dalton.

And in one embodiment, in order to increase hydrophobicity of the hydrophobic B block for improving the stability of the nanoparticle, the hydrophobic block B may be modified by chemically bonding tocopherol, cholesterol or a fatty acid having 10 to 24 carbon atoms to a hydroxyl group at the terminal thereof.

In one embodiment, the content of the amphiphilic block copolymer including the hydrophilic block (A) and the hydrophobic block (B) in the composition may be, for example, 150 parts by weight or less, 100 parts by weight or less, 70 parts by weight or less, 50 parts by weight or less or 30 parts by weight or less, and may be 1 part by weight or more, 10 parts by weight or more or 15 parts by weight or more, based on 1 part by weight of the active ingredient. For example, the content of the amphiphilic block copolymer in the composition may be 1 to 150 parts by weight, 10 to 100 parts by weight, 10 to 70 parts by weight, 15 to 50 parts by weight or 15 to 30 parts by weight, based on 1 part by weight of the active ingredient. If the content of the amphiphilic block copolymer in the composition is less than the above range, the size of the nanoparticles becomes too large, the stability of the nanoparticles is reduced, and there is a risk that the loss rate during filter sterilization may increase. If the content of the amphiphilic block copolymer exceeds the above range, the content of the active ingredient that can be incorporated is too small.

In one embodiment, regarding the ratio of the hydrophilic block (A) and the hydrophobic block (B) in the amphiphilic block copolymer, the ratio of the hydrophilic block (A) may be 40 to 70 wt %, and specifically 50 to 60 wt %, based on total weight of the copolymer. If the ratio of the hydrophilic block (A) is less than 40 wt %, solubility of the polymer in water is low, and thus it may be difficult to form a nanoparticle. Therefore, the ratio of the hydrophilic block (A) is preferably no less than 40 wt % to give sufficient water solubility for the copolymer to form a nanoparticle. If the ratio of the hydrophilic block (A) exceeds 70 wt % based on total weight of the copolymer, hydrophilicity may be too high and thus stability of the polymeric nanoparticle may become too low, and it may be difficult to use it as a solubilizing composition of the active ingredient/cationic compound complex. Therefore, in light of the stability of the nanoparticle, the ratio of the hydrophilic block (A) is preferably no more than 70 wt %.

In one embodiment, the amphiphilic block copolymer allows enclosure of the complex of the active ingredient and the cationic compound in the nanoparticle structure in an aqueous solution, wherein the ratio of the weight of the complex of the active ingredient and the cationic compound (a) to the weight of the amphiphilic block copolymer (b) [a/b×100; (the weight of the active ingredient + the weight of the cationic compound)/the weight of the amphiphilic block copolymer×100] may be 90% or less, 80% or less, 60% or less, 50% or less or 45% or less, and may be 1% or more, 2% or more, 5% or more, 10% or more, 15% or more, 20% or more, 21% or more or 25% or more—for example, 1 to 90%, 2 to 50%, 10 to 50%, 15 to 50%, or 21% to 45%. If the weight ratio (a/b×100) is less than 1%, the content of the complex of the active ingredient and the cationic compound may become too low, and thus it may be difficult to meet the effective content that the active ingredient can effectively act on. If it exceeds 60%, a nanoparticle structure of appropriate size may not be formed considering the molecular weight of the amphiphilic block copolymer and the amount of the complex of the active ingredient and the cationic compound.

The nanoparticle structure in the composition according to the present invention comprises a salt of polylactic acid (e.g., sodium polylactate (PLANa)). The salt of polylactic acid is distributed to the core (inner wall) of the nanoparticle so as to enhance hydrophobicity of the core and stabilize the nanoparticle, and at the same time, help evade reticuloendothelial system (RES) efficiently in the body. That is, an anion of carboxylic acid in the salt of polylactic acid efficiently binds to the cationic complex so as to decrease the surface charge of the polymeric nanoparticle. Thereby, positive charge of the surface potential of a polymeric nanoparticle would be less than that of a polymeric nanoparticle that does not contain a salt of polylactic acid, and thus it may be less captured by the reticuloendothelial system and efficiently delivered to target sites (e.g., cancer cells, inflammatory cells, etc.).

In one embodiment, the salt of polylactic acid, which is an independent component from the amphiphilic block copolymer, is a component of an inner wall of the nanoparticle and may have a number average molecular weight of 500 to 50,000 Dalton, and specifically 1,000 to 50,000 Dalton. If the number average molecular weight is less than 500 Dalton, the salt of polylactic acid does not easily exist at the core (inner wall) of the nanoparticle because the hydrophobicity is too low. If the number average molecular weight exceeds 50,000 Dalton, the polymeric nanoparticle may be too big.

In one embodiment, the content of the salt of polylactic acid in the composition may be 80 parts by weight or less, 60 parts by weight or less, 50 parts by weight or less, 40 parts by weight or less or 30 parts by weight or less, and may be 1 part by weight or more, 5 parts by weight or more, 10 parts by weight or more, 15 parts by weight or more or 20 parts by weight or more based on 1 part by weight of the active ingredient. For example, the content of the salt of polylactic acid in the composition may be 1 to 80 parts by weight, 1 to 50 parts by weight, 1 to 40 parts by weight, 5 to 30 parts by weight or 20 to 60 parts by weight based on 1 part by weight of the active ingredient. If the content of the salt of polylactic acid in the composition is less than the above range, the delivery efficiency of the active ingredient may decrease. If the content of the salt of polylactic acid exceeds the above range, the nanoparticles may become too large, so that filtration using a sterile membrane may be difficult or stability may be reduced. In one embodiment, the terminal opposite to the metal carboxylate (e.g., sodium carboxylate) among the terminals of the salt of polylactic acid (e.g., sodium polylactate) may be substituted with one selected from the group consisting of hydroxy, acetoxy, benzoyloxy, decanoyloxy, palmitoyloxy and alkoxy having 1 or 2 carbon atoms.

In one embodiment, the salt of polylactic acid may be selected from the group consisting of Formulae 2 to 7 as below.

$RO—CHZ—[A]_n—[B]_m—COOM$ [Formula 2]

In Formula 2, A is —COO—CHZ—; B is —COO—CHY—, —COO—$CH_2CH_2CH_2CH_2CH_2$— or —COO—$CH_2CH_2OCH_2$; R is a hydrogen atom, or acetyl, benzoyl, decanoyl, palmitoyl, methyl or ethyl group; each of Z and Y is a hydrogen atom, or methyl or phenyl group; M is Na, K or Li; n is an integer from 1 to 30; and m is an integer from 0 to 20;

$RO—CHZ—[COO—CHZ]_p—[COO—CHY']_q—COO—CHZ—COOH$ [Formula 3]

In Formula 3, X is methyl group; Y' is a hydrogen atom or phenyl group; p is an integer from 0 to 25, q is an integer from 0 to 25, with the proviso that p+q is an integer from 5 to 25; R is a hydrogen atom, or acetyl, benzoyl, decanoyl, palmitoyl, methyl or ethyl group; M is Na, K or Li; and Z is a hydrogen atom, methyl or phenyl group;

RO-PAD-COO—W-M' [Formula 4]

In formula 4, W-M' is

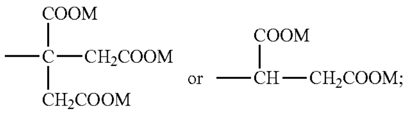

PAD is selected from the group consisting of D,L-polylactide, D-polylactide, polymandelic acid, copolymer of D,L-lactide and glycolic acid, copolymer of D,L-lactide and mandelic acid, copolymer of D,L-lactide and caprolactone, and copolymer of D,L-lactide and 1,4-dioxane-2-one; R is a hydrogen atom, or acetyl, benzoyl, decanoyl, palmitoyl, methyl or ethyl group; and M is independently Na, K or Li;

S—O-PAD-COO-Q [Formula 5]

In Formula 5, S is

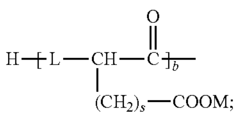

L is —$NR_1$— or —O—, wherein $R_1$ is a hydrogen atom or $C_{1-10}$ alkyl; Q is $CH_3$, $CH_2CH_3$, $CH_2CH_2CH_3$, $CH_2CH_2CH_2CH_3$ or $CH_2C_6H_5$; a is an integer from 0 to 4; b is an integer from 1 to 10; M is Na, K or Li; and PAD is at least one selected from the group consisting of D,L-polylactide, D-polylactide, polymandelic acid, copolymer of D,L-lactide and glycolic acid, copolymer of D,L-lactide and mandelic acid, copolymer of D,L-lactide and caprolactone, and copolymer of D,L-lactide and 1,4-dioxane-2-one;

[Formula 6]

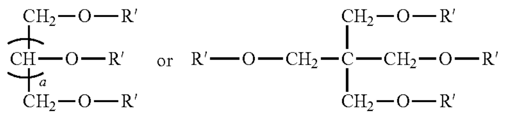

In Formula 6, R' is -PAD-O—C(O)—$CH_2CH_2$—C(O)—OM, wherein PAD is selected from the group consisting of D,L-polylactide, D-polylactide, polymandelic acid, copolymer of D,L-lactide and glycolic acid, copolymer of D,L-lactide and mandelic acid, copolymer of D,L-lactide and caprolactone, and copolymer of D,L-lactide and 1,4-dioxane-2-one, M is Na, K or Li; and a is an integer from 1 to 4; and $YO—[—C(O)—(CHX)_a—O—]_m—C(O)—R—C(O)—[—O—(CHX')_b—C(O)—]_n—OZ$ [Formula 7]

In Formula 7, X and X' are independently hydrogen, $C_{1-10}$ alkyl or $C_{6-20}$ aryl; Y and Z are independently Na, K or Li; m and n are independently an integer from 0 to 95, with the proviso that $5<m+<100$; a and b are independently an integer from 1 to 6; and R is —$(CH_2)_k$—, $C_{2-10}$ divalent alkenyl, $C_{6-20}$ divalent aryl or a combination thereof, wherein k is an integer from 0 to 10.

In one embodiment, the salt of polylactic acid may be the compound of Formula 2 or Formula 3.

In one embodiment, the composition of the present invention may further comprise a fusogenic lipid in an amount of 0.01 to 50 wt %, and specifically 0.1 to 10 wt % based on total weight of the composition, for increasing delivery efficiency of mRNA into cells.

The fusogenic lipid forms a complex of mRNA, the cationic lipid and the fusogenic lipid by binding due to a hydrophobic interaction when it is mixed with the complex of mRNA and the cationic lipid. The complex containing the fusogenic lipid is entrapped in the nanoparticle structure of the amphiphilic block copolymer.

In one embodiment, the fusogenic lipid may be one or a combination of two or more selected from the group consisting of phospholipid, cholesterol and tocopherol.

More specifically, the phospholipid may be at least one selected from the group consisting of phosphatidylethanolamin (PE), phosphatidylcholine (PC) and phosphatidic acid. The phosphatidylethanolamin (PE), phosphatidylcholine (PC) and phosphatidic acid may be in a form combined with one or two $C_{10-24}$ fatty acids. The cholesterol and tocopherol may include analogues, derivatives and metabolites of each of cholesterol and tocopherol.

Much more specifically, the fusogenic lipid may be one or a combination of two or more selected from the group consisting of dilauroyl phosphatidylethanolamine, dimyristoyl phosphatidylethanolamine, dipalmitoyl phosphatidylethanolamine, distearoyl phosphatidylethanolamine, dioleoyl phosphatidylethanolamine, dilinoleoyl phosphatidylethanolamine, 1-palmitoyl-2-oleoyl phosphatidylethanolamine, 1,2-diphytanoyl-3-sn-phosphatidylethanolamine, dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, 1,2-diphytanoyl-3-sn-phosphatidylcholine, dilauroyl phosphatidic acid, dimyristoyl phosphatidic acid, dipalmitoyl phosphatidic acid, distearoyl phosphtidic acid, dioleoyl phosphatidic acid, dilinoleoyl phosphatidic acid, 1-palmitoyl-2-oleoyl phosphatidic acid, 1,2-diphytanoyl-3-sn-phosphatidic acid, cholesterol and tocopherol.

Much more specifically, the fusogenic lipid may be at least one selected from the group consisting of dioleoyl phosphatidylethanolamine (DOPE), 1,2-dipalmitoleoyl-sn-glycero-3-phosphocholine (DPPC), 1,2-dioleoyl-sn-glycero-3-phosphocholine (DOPC) and 1,2-dipalmitoleoyl-sn-glycero-3-phosphoethanolamine (DPPE).

In an embodiment, the composition of the present invention may further comprise divalent or trivalent metal ion.

The divalent or trivalent metal ion may be preferably selected from calcium ($Ca^{2+}$), magnesium ($Mg^{2+}$), barium ($Ba^{2+}$), chromium ($Cr^{3+}$), iron ($Fe^{3+}$), manganese ($Mn^{2+}$), nickel ($Ni^{2+}$), copper ($Cu^{2+}$), zinc ($Zn^{2+}$) or aluminum ($Al^{3+}$), etc.

The metal ion may be added to the polymer nanoparticle composition in a form of sulfate salt, chloride salt, carbonate salt, phosphate salt or hydroxide. Preferably, it may be added in a form of calcium chloride ($CaCl_2$), magnesium chloride ($MgCl_2$), zinc chloride ($ZnCl_2$), aluminum chloride ($AlCl_3$), ferric chloride ($FeCl_3$), calcium carbonate ($CaCO_3$), magnesium carbonate ($MgCO_3$), calcium phosphate ($Ca_3(PO_4)_2$), magnesium phosphate ($Mg_3(PO_4)_2$), aluminum phosphate ($AlPO_4$), magnesium sulfate ($MgSO_4$), calcium hydroxide ($Ca(OH)_2$), magnesium hydroxide ($Mg(OH)_2$), aluminum hydroxide ($Al(OH)_3$), zinc hydroxide ($Zn(OH)_2$) or a mixture thereof.

By controlling the amount of equivalent of the divalent or trivalent metal ion, the release rate of drug entrapped in the polymer nanoparticle can be controlled. Concretely, if the divalent or trivalent metal ion is contained in the polymer nanoparticle composition in an amount of 1 equivalent or less to the equivalent of the carboxyl group of the salt of polylactic acid, the number thereof binding to the carboxyl terminal group of the salt of polylactic acid is small and the release rate of drug increases, and if it is contained in an amount of 1 equivalent or more, the number thereof binding to the carboxyl terminal group of the salt of polylactic acid is large and the drug release is sustained. Thus, in order to increase the release rate of drug in blood, less equivalent of metal ion may be used, whereas in order to sustain the drug release, more equivalent of metal ion may be used.

Also, the divalent or trivalent metal ion may be contained in amount of 0.01 to 10 equivalents, 0.1 to 5 equivalents or 0.2 to 2 equivalents, to the equivalent of the carboxyl terminal group of the salt of polylactic acid.

In a specific embodiment, the composition of the present invention, which contains the active ingredient-cationic compound complex entrapped in the nanoparticle structure of the amphiphilic block copolymer and the salt of polylactic acid, may be administered by the route of blood vessel, muscle, subcutaneous, oral, bone, transdermal or local tissue, and the like, and it may be formulated into various oral or parenteral administration formulations. Examples of the oral administration formulation may include tablets, capsules, powder and liquid, and examples of the parenteral administration formulation may include eye drop and injection. In one preferred embodiment, the composition may be a formulation for injection. For example, if the compound is lyophilized, it may be reconstituted with distilled water for injection, 0.9% physiological saline, 5% dextrose aqueous solution, and the like, to formulate into an injection formulation.

In one embodiment, the composition for inducing immunity may be used for treating or preventing cancer. The composition for inducing immunity can efficiently deliver an active ingredient to the spleen. In this process, even if it is an autoantigen that is difficult to recognize as an antigen during simple administration, the composition induces immunity to the antigen so that the same effect as a vaccine can be expected. Therefore, in one embodiment, the composition for inducing immunity may be one that targets the spleen. These effects can be obtained not only by local administration but also by systemic administration.

Another aspect of the present invention provides a method for preparing a composition for inducing immunity to the active ingredient, comprising (a) mixing a nucleic acid, a polypeptide or a combination thereof as the active ingredient, a cationic compound, an amphiphilic block copolymer and a salt of polylactic acid with a solvent which is an aqueous solution, a water-miscible organic solvent or a combination thereof; and (b) adding an aqueous solvent to the mixture of step (a) and mixing them.

Step (a) may comprise the steps of (a-1) mixing an aqueous solution containing an active ingredient, which is a nucleic acid, a polypeptide or a combination thereof, with a solution in which a cationic compound is dissolved in a water-miscible organic solvent; and (a-2) mixing an aqueous solution of the amphiphilic block copolymer and a salt of polylactic acid with the mixture of step (a-1).

Alternatively, step (a) may further comprise the steps of (a-1) mixing an aqueous solution containing an active ingredient that is a nucleic acid, a polypeptide or a combination thereof with an aqueous solution containing a salt of polylactic acid; and (a-2) mixing the mixture of step (a-1) with a water-miscible organic solvent containing a cationic compound and an aqueous solution containing an amphiphilic block copolymer.

The preparation method may further include a step of removing the solvent from the mixture of step (b).

The "aqueous solution" may refer to, for example, water, sterile purified water, buffer solution, injection solution, etc., and may be a buffer solution further containing an organic acid. The aqueous solution may be, for example, a citric acid buffer, a PBS buffer and the like, but it is not limited thereto.

The "water-miscible organic solvent" may be alcohol, acetone, acetonitrile, a water mixture thereof or a mixture thereof, but it is not limited thereto.

According to another embodiment, the preparing method may further comprise a step of lyophilizing by adding a lyophilization aid after the step of removing the solvent.

According to another embodiment, the preparing method may further comprise a step of sterilizing the polymer nanoparticle aqueous solution with a sterilizing filter before lyophilizing.

The lyophilization aid used in the present invention is added to help the lyophilized composition maintain a form of cake, or to help the amphiphilic block copolymer composition melt quickly and evenly during the reconstitution process after lyophilization of the composition. Specifically, the lyophilization aid may be at least one selected from the group consisting of lactose, mannitol, sorbitol and sucrose. The amount of the lyophilization aid may be 1 to 90 wt %, and more specifically 10 to 60 wt %, based on the total dry weight of the lyophilized composition.

Nanoparticles in the composition prepared by the preparing method according to the present invention, in which the active ingredient and the cationic compound complex are entrapped in the nanoparticle structure of the amphiphilic block copolymer and the salt of polylactic acid, are stable in blood, and their size may be specifically 10 to 200 nm, more specifically 10 to 150 nm.

DETAILED DESCRIPTION TO CARRY OUT THE INVENTION

Hereinafter, the present invention will be explained in detail with reference to the following Examples. However, these Examples are only meant to illustrate the invention and its scope are not limited thereto in any manner.

[Examples 1 and 2] Preparation of a composition for Inducing Immunity Comprising Tumor Antigen-Expressing mRNA as an Active Ingredient 100 μl of Trp2 mRNA (TriLink, cat # L7008, 10 mM citrate buffer, 1 mg/ml) and 76.4 μl of PLANa aqueous solution (10 mg/ml) were prepared and mixed. Then, 30 μl of a cationic lipid 2OT(N,N'-((ethane-1,2-diylbis (azanediyl))bis(ethane-2,1-diyl))dioleamide) solution (20 mM sodium acetate buffer, 20 mg/ml) and 166 μl of aqueous solution of mPEG-PLA (10 mg/ml) were mixed and put into the prepared Trp2 mRNA and PLANa mixed solution to form a complex. Thereafter, PBS was filled to a concentration of 10 μg/200 μl of mRNA, and filtered through a 0.22 μm PVDF filter to exclude formulations with large particles.

TABLE 1

| | Comparative Example 1 | Example 1 | Example 2 | Comparative Example 2 |
|---|---|---|---|---|
| mRNA (μg) | 10 | 10 | 10 | 10 |
| 20T (μg) | 10 | 40 | 60 | 250 |
| mPEG-PLA (μg) | 100 | 200 | 166 | 1500 |
| PLANa (μg) | 10 | 150 | 72 | 500 |

mPEG-PLA: Monomethoxy polyethylene glycol-polylactide block copolymer
PLANa: Sodium polylactate

[Experimental Example 2] Confirmation of Protein Expression after Intravenous Injection of a Composition for Inducing Immunity in Mice The compositions for inducing immunity of Examples 1 and 2 were administered to the hind legs of mice using PBS buffer as a carrier. After administration three times on days 0, 7 and 14, mice were sacrificed on day 20, spleens were collected, and spleen cells were isolated. Splenocytes were extracted from the spleen, and the tissue was put into a 40 μm cell strainer and then homogenized using the tip of a syringe plunger. 5 ml of serum-free medium was added and centrifuged (1,200 rpm, 5 min, 4° C.). After removing the supernatant, 1 ml of red blood cell lysis solution was added. After reacting at room temperature for about 3 minutes, 1 ml of PBS was added to neutralize the reaction. The mixture was centrifuged (1,200 rpm, 5 min, 4° C.), suspended in 1 ml culture medium and stored on ice. After staining with 0.4% trypan blue solution, live splenocytes were counted using a hemocytometer.

In order to ascertain whether IFN-γ was expressed for each test group and control group, it was shown graphically as ELISPOT. Specifically, $5\times10^5$ to $1\times10^6$ splenocytes were placed in an ELISPOT plate, and OVA peptide (10 μg/ml) was added as a stimulant. After reacting for 36 hours in a 37° C. wet incubator under 5% $CO_2$ conditions, IFN-γ expression was measured using a detection antibody for IFN-γ and streptavidin-ALP, and was shown by graph. Among splenocytes, IFN-γ secretion is mostly considered to be a result of activation of T-cells that recognize antigenic epitopes.

As a control group, PBS carrier and free mRNA which is not processed into nanoparticles were administered, respectively. TransIT®, a commercially available transfection reagent, was used as a comparison group, and Trp2 peptide and I:C (Polyinosinic:polycytidylic acid) were subcutaneously administered as a positive control group. 'I:C' is known to act as an immune adjuvant by stimulating TLR3 (toll-like receptor) expressed on the cell surface of B-cells, macrophages and dendritic cells. Therefore, when it is used together with the antigenic substance Trp2, immune activity is induced, so it is suitable as a positive control. Table 2 below summarizes the test group and antigenic substance (mRNA) dose for each test group.

TABLE 2

| Test group | Number of individuals | Dose |
|---|---|---|
| PBS | 2 | N/A |
| Free mRNA | 5 | 10 μg |
| Example 2(mSENS) I | 9 | 10 μg |
| Example 2(mSENS) II | 9 | 20 μg |
| TransIT ® | 9 | 10 μg |
| Trp2 peptide + poly (I:C) | 6 | 100 + 50 μg |

The results are shown in FIGS. 3 and 4. As a result of observation of IFN-γ expression, strong IFN-γ was detected in the group administered with the composition for inducing immunity of Examples 1 and 2, and in the positive control group.

[Experimental Example 3] Confirmation of Mouse Splenocyte Expression Rate of the Composition for Induction of Immunity The composition for induction of immunity was prepared in the same manner as in Example 2, except that instead of the mRNA expressing Trp2, an mRNA capable of expressing luciferase (luc: Trilink, cat #L7202) was introduced (Example 3). 10 μg mRNA of Example 3, Comparative Example 1 having smaller N/P (nitrogen-to-phosphate) ratio and Comparative Example 2 having larger N/P ratio were administered to the tail vein of the mouse (BALB/cAnNCrlOri, n=3). Six hours after administration, mice were sacrificed, and each organ was removed to measure the luminescence expression pattern (L=liver, S=spleen, H=heart, Lu=lung, and K=kidney).

As a result, as shown in FIG. 5, it was confirmed that the expression was significantly higher in the spleen compared to other organs.

[Experimental Example 4] Confirmation of the Cancer Treatment Effect of the Composition for Inducing Immunity The composition for inducing immunity of Example 2 was used. In mice (BALB/cAnNCrlOri, n=3), melanoma cells B16F10 cells at $2.5\times10^5$ cells were intravenously administered. On the 3rd day, PBS was used as a carrier in the tail vein, and 10 μg of mRNA was administered on the 3rd, 5th, 7th and 9th days for immunization. After sacrifice on the 19th day, metastasis to the lung nodule was observed.

As a control group, those administered only with PBS as a carrier and those administered only with mRNA were used. One-way ANOVA post-hoc Tukey's multiple comparison for the number of lung nodules showed statistical values as shown in FIG. 6 (*p<0.001, **p<0.0001 vs. mRNA).

As a result, it was observed that the lung metastasis of the composition for inducing immunity of the present invention was significantly lower than that of the control group, confirming the cancer treatment effect according to inducing immunity.

All of the above animal experiments were conducted according to protocols approved by the Institutional Animal Care and Use Committee (IACUC).

The invention claimed is:

1. A method for inducing immunity to an active ingredient, comprising administering to a subject a composition which comprises:

a nucleic acid as the active ingredient;

a cationic compound represented by the following Formula 1; an A-B type block copolymer including a hydrophilic A block of alkylene glycol and a hydrophobic B block of polyester as an amphiphilic block copolymer; and a salt of polylactic acid, wherein a content of the cationic compound is 2 to 15 parts by weight, a content of the amphiphilic block copolymer is 15 to 50 parts by weight, and a content of the salt of polylactic acid is 5 to 30 parts by weight, based on 1 part by weight of the active ingredient;

wherein the active ingredient is entrapped in a nanoparticle structure of the amphiphilic block copolymer and the salt of polylactic acid, wherein the composition is suitable for delivering the active ingredient to the spleen efficiently; and wherein the composition is suitable for treating cancer by inducing immunity to the active ingredient:

[Formula 1]

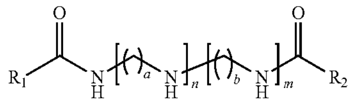

in Formula 1, each of n and m is independently 1 to 9, and $2 \leq n+m \leq 10$, each of a and b is 2 to 4, each of $R_1$ and $R_2$ is independently selected from the group consisting of lauryl, myristyl, palmityl, stearyl, arachidyl, behenyl, lignoceryl, cerotyl, myristoleyl, palmitoleyl, sapienyl, oleyl, linoleyl, arachidonyl, eicosapentaenyl, erucyl, docosahexaenyl and cerotyl.

2. The method for inducing immunity according to claim 1, wherein the nucleic acid expresses a tumor antigen.

3. The method for inducing immunity according to claim 2, which is for treating a disease related to the tumor antigen.

4. The method for inducing immunity according to claim 2, which is for use as a vaccine against a disease related to the tumor antigen.

5. The method for inducing immunity according to claim 1, wherein a surface charge of the nanoparticles is −40 to 40 mV.

6. The method for inducing immunity according to claim 1, wherein the hydrophobic block B is modified by chemically bonding tocopherol, cholesterol or a fatty acid having 10 to 24 carbon atoms to a hydroxyl group at a terminal thereof.

7. The method for inducing immunity according to claim 1, wherein the hydrophilic A block has a number average molecular weight of 200 to 50,000 Dalton, and the hydrophobic B block has a number average molecular weight of 50 to 50,000 Dalton.

8. The method according to claim 1, wherein:

said cationic compound is at least one member selected from the group consisting of 1,6-triethylenetetramide (N,N'-((ethane-1,2-diylbis(azanediyl))bis(ethane-2,1-dioleoyl diyl))dioleamide), 1,8-dilinoleoyl tetraethylenepentamide ((9Z,9'Z,12Z,12'Z)—N,N'-(((azanediylbis(ethane-2,1-diyl))bis(azanediyl))bis(ethane-2,1-diyl))bis(octadeca-9,12-dienamide)), 1,4-dimyristoleoyl diethylenetriamide((9Z,9'Z)—N,N'-(azanediylbis(ethane-2,1-diyl))bis(tetradec-9-enamide)), 1,10-distearoyl pentaethylenehexamide (N,N'-(3,6,9,12-tetraazatetradecane-1,14-diyl)distearamide) and 1,10-dioleoyl pentaethylenehexamide (N,N'-(3,6,9,12-tetraazatetradecanc-1,14-diyl)dioleamide);

said hydrophilic A block is at least one member selected from the group consisting of polyalkyleneglycol, polyvinyl alcohol, polyvinyl pyrrolidone, polyacrylamide and derivatives thereof; and said hydrophobic B block is at least one member selected from the group consisting of polylactide, polyglycolide, polycaprolactone, polydioxane-2-one, a copolymer of polylactide and glycolide, a copolymer of polylactide and polydioxane-2-one, a copolymer of polylactide and polycaprolactone, and a copolymer of polyglycolide and polycaprolactone.

9. The method according to claim 1, wherein:

said cationic compound is N,N'-((ethane-1,2-diylbis(azanediyl))bis(ethane-2,1-diyl))dioleamide;

said A-B type block copolymer is monomethoxy polyethylene glycol-polylactide block copolymer; and said salt of polylactic acid is sodium polylactate.

10. A method for preparing a composition for inducing immunity to an active ingredient, comprising (a) mixing a nucleic acid as the active ingredient, a cationic compound represented by the following Formula 1, an A-B type block copolymer including a hydrophilic A block of alkylene glycol and a hydrophobic B block of polyester as an amphiphilic block copolymer and a salt of polylactic acid with a solvent which is an aqueous solution, a water-miscible organic solvent or a combination thereof; and (b) adding an aqueous solvent to the mixture of step (a) and mixing them, wherein a mixing amount of the cationic compound is 2 to 15 parts by weight, a mixing amount of the amphiphilic block copolymer is 15 to 50 parts by weight, and a mixing amount of the salt of polylactic acid is 5 to 30 parts by weight, based on 1 part by weight of the active ingredient;

wherein the active ingredient is entrapped in a nanoparticle structure of the amphiphilic block copolymer and the salt of polylactic acid;

wherein the composition is suitable for delivering the active ingredient to the spleen efficiently; and wherein the composition is suitable for treating cancer by inducing immunity to the active ingredient:

[Formula 1]

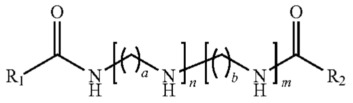

in Formula 1, each of n and m is independently 1 to 9, and 2≤n+m≤10, each of a and b is 2 to 4, each of $R_1$ and $R_2$ is independently selected from the group consisting of lauryl, myristyl, palmityl, stearyl, arachidyl, behenyl, lignoceryl, cerotyl, myristoleyl, palmitoleyl, sapienyl, oleyl, linoleyl, arachidonyl, eicosapentaenyl, erucyl, docosahexaenyl and cerotyl.

11. A method for treating cancer by efficiently delivering a nucleic acid to the spleen and inducing immunity to a tumor antigen, comprising administering to a subject a composition which comprises:

a nucleic acid that expresses a tumor antigen;

a cationic compound represented by the following Formula 1;

an A-B type block copolymer including a hydrophilic A block of alkylene glycol and a hydrophobic B block of polyester as an amphiphilic block copolymer; and a salt of polylactic acid, wherein a content of the cationic compound is 2 to 15 parts by weight, a content of the amphiphilic block copolymer is 15 to 50 parts by weight, and a content of the salt of polylactic acid is 5 to 30 parts by weight, based on 1 part by weight of the nucleic acid;

wherein the nucleic acid is entrapped in a nanoparticle structure of the amphiphilic block copolymer and the salt of polylactic acid:

[Formula 1]

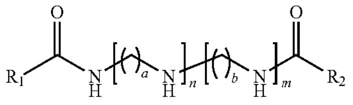

in Formula 1, each of n and m is independently 1 to 9, and 2≤n+m≤10, each of a and b is 2 to 4, each of $R_1$ and $R_2$ is independently selected from the group consisting of lauryl, myristyl, palmityl, stearyl, arachidyl, behenyl, lignoceryl, cerotyl, myristoleyl, palmitoleyl, sapienyl, oleyl, linoleyl, arachidonyl, eicosapentaenyl, erucyl, docosahexaenyl and cerotyl.

12. The method according to claim 11, wherein said tumor antigen is a member selected from the group consisting of Trp2 (tyrosinase-related protein 2), gp100 (Glycoprotein 100), tyrosinase, PSA (Prostate-specific antigen), WT1 (Wilms' tumor 1), MAGE-1 (Melanoma-associated antigen 1), NY-ESO-1 (cancer-testis antigen), and MUC-1 (Mucin 1).

13. The method according to claim 11, wherein:

said cationic compound is at least one member selected from the group consisting of 1,6-dioleoyl triethylenetetramide (N,N'-((ethane-1,2-diylbis(azanediyl))bis(ethane-2,1-diyl))dioleamide), 1,8-dilinoleoyl tetraethylenepentamide ((9Z,9'Z,12Z,12'Z)—N,N'-(((azanediylbis(ethane-2,1-diyl))bis(azanediyl))bis(ethane-2,1-diyl))bis(octadeca-9,12-dienamide)), 1,4-dimyristoleoyl diethylenetriamide((9Z,9'Z)—N,N'-(azanediylbis(ethane-2,1-diyl))bis(tetradec-9-enamide)), 1,10-distearoyl pentaethylenehexamide (N,N'-(3,6,9,12-tetraazatetradecane-1,14-diyl)distearamide) and 1,10-dioleoyl pentaethylenehexamide (N,N'-(3,6,9,12-tetraazatetradecane-1,14-diyl)dioleamide);

said hydrophilic A block is at least one member selected from the group consisting of polyalkyleneglycol, polyvinyl alcohol, polyvinyl pyrrolidone, polyacrylamide and derivatives thereof; and said hydrophobic B block is at least one member selected from the group consisting of polylactide, polyglycolide, polycaprolactone, polydioxane-2-one, a copolymer of polylactide and glycolide, a copolymer of polylactide and polydioxane-2-one, a copolymer of polylactide and polycaprolactone, and a copolymer of polyglycolide and polycaprolactone.

14. The method according to claim 11, wherein:

said cationic compound is N,N'-((ethane-1,2-diylbis(azanediyl))bis(ethane-2,1-diyl))diolcamide;

said A-B type block copolymer is monomethoxy polyethylene glycol-polylactide block copolymer; and said salt of polylactic acid is sodium polylactate.

15. The method according to claim 14, wherein a surface charge of the nanoparticles is −40 to 40 m V.

16. The method for inducing immunity according to claim 11, wherein a surface charge of the nanoparticles is-40 to 40 mV.

* * * * *